(12) United States Patent
Hunter

(10) Patent No.: US 10,398,596 B2
(45) Date of Patent: Sep. 3, 2019

(54) METHOD FOR USING MICROELECTROMECHANICAL SYSTEMS TO GENERATE MOVEMENT IN A PHACOEMULSIFICATION HANDPIECE

(71) Applicant: Abbott Medical Optics Inc., Santa Ana, CA (US)

(72) Inventor: Timothy Hunter, Irvine, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 0 days.

(21) Appl. No.: 13/917,436

(22) Filed: Jun. 13, 2013

(65) Prior Publication Data

US 2013/0282020 A1 Oct. 24, 2013

Related U.S. Application Data

(63) Continuation of application No. 13/043,022, filed on Mar. 8, 2011, now abandoned.
(Continued)

(51) Int. Cl.
*A61F 9/007* (2006.01)

(52) U.S. Cl.
CPC ...... *A61F 9/00745* (2013.01); *A61F 9/00763* (2013.01)

(58) Field of Classification Search
CPC .. A61F 9/007; A61F 9/00709; A61F 9/00736; A61F 9/00745; A61F 9/00754; A61F 9/00763
(Continued)

(56) References Cited

U.S. PATENT DOCUMENTS 5,728,089 A 3/1998 Lal et al.
5,733,256 A 3/1998 Costin
(Continued)

FOREIGN PATENT DOCUMENTS

WO 2007056763 A2 5/2007

OTHER PUBLICATIONS

Cedrat, Amplified Piezoelectric Actuators [online], 2009 [retrieved on Jun. 10, 2011]. Retrieved from the Internet< URL: http://web.archieve.org/web/20090422023915/http://www.cedrat.com/en/mechatronic-products/actuators/apa.html>.
(Continued)

*Primary Examiner* — David C Eastwood
(74) *Attorney, Agent, or Firm* — Johnson & Johnson Surgical Vision, Inc.

(57) ABSTRACT

The present invention relates to a phacoemulsification handpiece, comprising a needle and a microelectromechanical system (MEMS) device, wherein the needle is coupled with the MEMS device. The phacoemulsification handpiece may further comprise a horn, wherein the horn is coupled with the needle and the MEMS device. The MEMS device is capable of generating movement of the needle in at least one direction, wherein at least one direction is selected from the group consisting of transversal, torsional, and longitudinal. The present invention also relates to a method of generating movement, comprising providing a phacoemulsification handpiece, wherein the handpiece comprises a needle and one or more MEMS devices; applying a voltage or current to the one or more MEMS devices, wherein the MEMS devices are coupled with the needle; and moving the needle in at least one direction. The present invention also relates to a vitrectomy cutter comprising one or more MEMS devices.

7 Claims, 5 Drawing Sheets

Related U.S. Application Data

(60) Provisional application No. 61/311,695, filed on Mar. 8, 2010.

(58) Field of Classification Search
USPC ....... 606/107, 127, 128, 161, 162, 166, 167, 606/169, 170, 171; 604/22
See application file for complete search history.

(56) References Cited

U.S. PATENT DOCUMENTS

| | | | |
|---|---|---|---|
| 5,843,109 A | 12/1998 | Mehta et al. | |
| 6,133,670 A * | 10/2000 | Rodgers | ................ B81B 3/0021 |
| | | | 310/309 |
| 6,575,990 B1 | 6/2003 | Wang et al. | |
| 6,638,249 B1 * | 10/2003 | Lal et al. | ...................... 604/151 |
| 6,852,092 B2 | 2/2005 | Kadziauskas et al. | |
| 7,169,123 B2 | 1/2007 | Kadziauskas et al. | |
| 2002/0193817 A1 | 12/2002 | Lal et al. | |
| 2004/0193198 A1 | 9/2004 | Cuny | |
| 2008/0114309 A1 | 5/2008 | Zuckerman | |
| 2009/0152980 A1 * | 6/2009 | Huang | .................. B06B 1/0238 |
| | | | 310/309 |
| 2009/0182365 A1 | 7/2009 | Cuny | |
| 2011/0125165 A1 * | 5/2011 | Simaan et al. | ................ 606/130 |
| 2011/0137330 A1 * | 6/2011 | Moreau-Gaudry et al. | .. 606/167 |

OTHER PUBLICATIONS

Chen X., et al., "integrated Pressure and Flow Sensor in Silicon-Based Ultrasonic Surgical Actuator," IEEE Ultrasonics Symposium, 2001, pp. 1373-1376.

International Search Report and Written Opinion for Application No. PCT/US2011/027547, dated Nov. 4, 2011, 18 pages.

Mottaghi M., et al., "Development of a Microsensor to Minimize Post Cataract Surgery Complications," World Academy of Sciences, Engineering and Technology, 2008, vol. 44, pp. 406-409.

Partial International Search Report for Application No. PCT/US2011/027547, dated Jul. 19, 2011, 4 pages.

* cited by examiner

METHOD FOR USING MICROELECTROMECHANICAL SYSTEMS TO GENERATE MOVEMENT IN A PHACOEMULSIFICATION HANDPIECE

CLAIM OF PRIORITY

The present application is a continuation application and claims priority to U.S. application Ser. No. 13/043,022, filed on Mar. 8, 2011, which is a nonprovisional application and claims priority under 35 U.S.C. § 119(e) to provisional application No. 61/311,695, filed on Mar. 8, 2010 under the same title, the entire contents of each is hereby incorporated by reference in its entirety for all purposes as if fully set forth herein. Full Paris Convention priority is hereby expressly reserved.

TECHNICAL FIELD OF THE INVENTION

The present invention relates to an ultrasound handpiece and in particular, generating movement of a tip of the handpiece using microelectromechanical systems (MEMS).

BACKGROUND OF THE INVENTION

During a phacoemulsification ("phaco") procedure, a needle of an ultrasound handpiece is placed within the capsular bag of an eye to emulsify the cataractic lens. The emulsified lens is removed from the eye and an intraocular lens ("IOL") is implanted. Ultrasound handpieces are driven by piezoelectric crystals or magnetostrictive drivers. Energy is applied to the piezoelectric crystals to vibrate the crystals to generate ultrasound energy, which is then transmitted through the needle of the handpiece into the cataractic lens. There are several theories as to how the cataractic lens is emulsified. One school of thought is that the ultrasound vibration causes cavitation, which in turn emulsifies the lens. Another school of thought is that the lens is emulsified by mere mechanical breakdown. Also, another school of thought is that it is a combination of cavitation and mechanical breakdown that emulsifies the cataractic lens. Despite these theories, there are several limitation placed on ultrasound handpieces when employing piezoelectric crystals. First, before each use the handpiece must be tuned, thereby lengthening the time of the procedure. Second, handpieces comprising piezoelectric crystals generate significant heat during use that may cause tissue damage. Third, the crystals add a significant amount of weight to the handpieces making them heavy and cumbersome to use and can cause fatigue for the doctors using such handpieces.

Based upon the foregoing, it would be advantageous to have a handpiece that is lighter, does not require tuning prior to use, and does not generate tissue damaging heat.

SUMMARY OF THE INVENTION

The present invention relates to a phaco handpiece, comprising a needle and a MEMS device, wherein the needle is coupled with the MEMS device. The phaco handpiece may further comprise a horn, wherein the horn is coupled with the needle and the MEMS device. The MEMS device is capable of generating movement of the needle in at least one direction, wherein at least one direction is selected from the group consisting of transversal, torsional, and longitudinal along a longitudinal axis of the needle. The phaco handpiece may further comprise a pad and a linkage, wherein the pad is coupled with the MEMS device via the linkage and the pad is coupled with the needle. The pad may be coupled with the needle via a linkage. The MEMS device may also be coupled with an outer surface of the needle.

The present invention also pertains to a method of generating movement, comprising providing a phaco handpiece, wherein the handpiece comprises a needle and one or more MEMS devices; applying a voltage or current to the one or more MEMS devices, wherein the MEMS devices are coupled with the needle; and moving the needle in at least one direction. The at least one direction may be selected from the group consisting of transversal, torsional, and longitudinal along a longitudinal axis of the needle.

The present invention also pertains to a vitrectomy cutter, comprising a needle body having one or more ports; a blade, wherein the blade is located within the needle body and capable of passing over the one or more ports; and a microelectromechanical system device, wherein the microelectromechanical device is coupled with the blade; wherein the microelectromechanical system device is capable of oscillating the blade.

BRIEF DESCRIPTION OF THE DRAWINGS

The present invention is best understood with reference to the following detailed description of the invention and the drawings in which.

DETAILED DESCRIPTION OF THE INVENTION

Reference will now be made in detail to embodiments of the invention, examples of which are illustrated in the accompanying drawings. While the invention will be described in conjunction with the embodiments, it will be understood that they are not intended to limit the invention to those embodiments. On the contrary, the invention is intended to cover alternatives, modifications, and equivalents, which may be included within the spirit and scope of the invention as defined by the appended claims.

Figure 1:
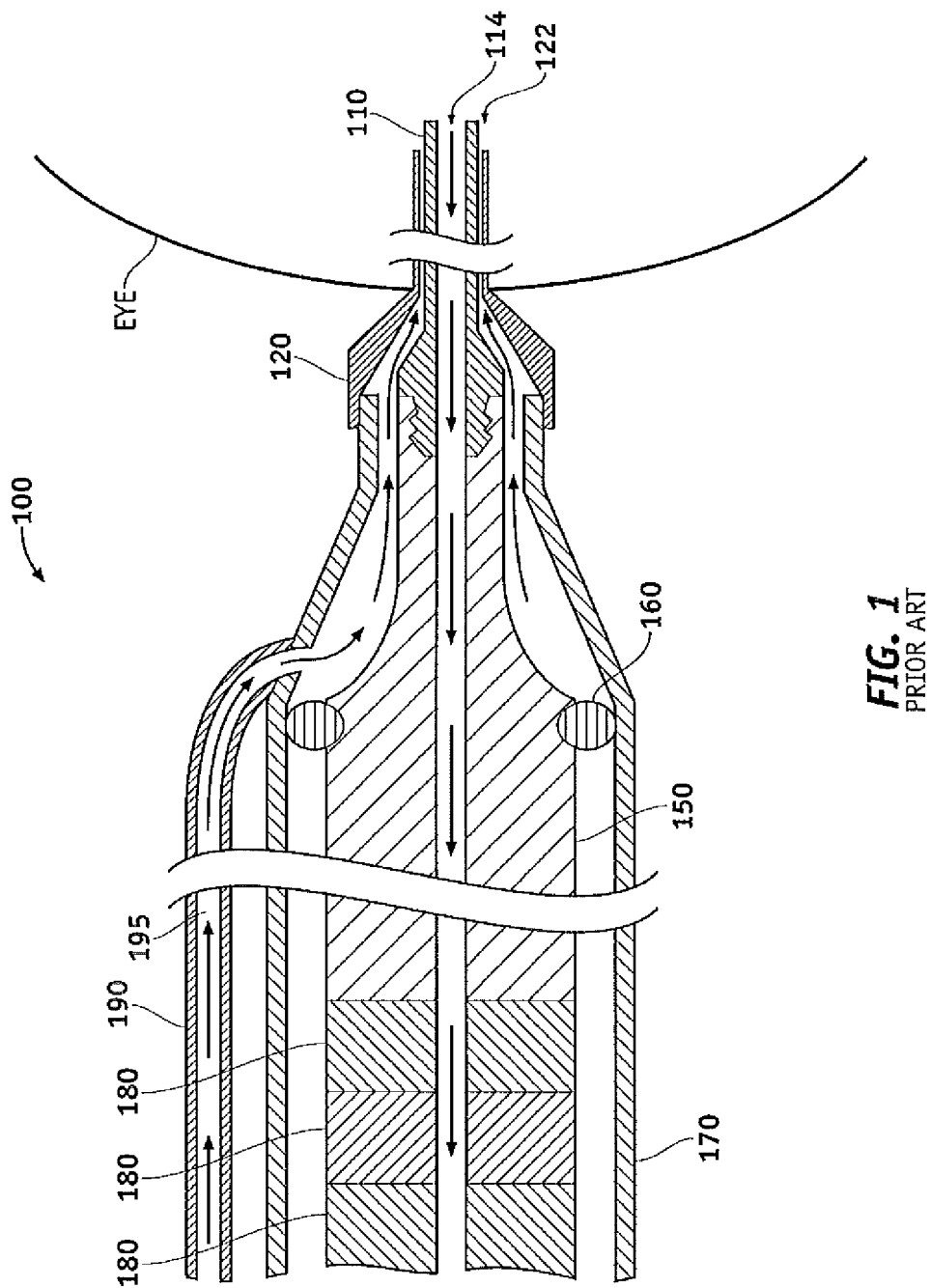
FIG. 1 is a cross-sectional view of an ultrasound phaco handpiece.

In FIG. 1 a cross-section along the longitudinal axis of a portion of an ultrasound phaco handpiece 100 known in the art is shown. Generally, handpiece 100 includes a needle 110, defining a lumen that is operatively coupled with an aspiration pump (not shown), forming an aspiration line 114. The proximal end of needle 110 is coupled with horn 150, which has its proximal end coupled with a set of piezoelectric crystals 180, shown as three rings. Horn 150, crystals 180, and a proximal portion of the needle 110 are enclosed within handpiece casing 170 having an irrigation port coupled with an irrigation line 190 defining an irrigation pathway 195. Irrigation line 190 is coupled with an irrigation source (not shown). Horn 150 is typically an integrated metal, such as titanium, structure and often includes a rubber O ring 160 around the mid-section, just before horn 150 tapers to fit with needle 110 at the distal end of horn 150. O ring 160 snugly fits between horn 150 and casing 170. O ring 160 seals the proximal portion of horn 150 from irrigation pathway 195. Thus, there is a channel of air defined between horn 150 and the casing 170. Descriptions of handpieces known in the art are provided in U.S. Pat. No. 6,852,092 (Kadziauskas, et al.) and U.S. Pat. No. 5,843,109 (Mehta, et al.), which are hereby incorporated by reference in their entirety.

In preparation for operation, sleeve 120 is typically added to the distal end of handpiece 100, covering the proximal portion of the needle 110 (thus, exposing the distal tip of the needle), and the distal end of irrigation pathway 195, thereby extending pathway 195 and defining an irrigation port 122 just before the distal tip of needle 110. Needle 110 and a portion of sleeve 120 are then inserted through the cornea of the eye to reach the cataractic lens.

During operation, irrigation path 195, the eye's chamber and aspiration line 114 form a fluidic circuit, where irrigation fluid enters the eye's chamber via irrigation path 195, and is then aspirated through aspiration line 114 along with other materials that the surgeon desires to aspirate out, such as the cataractic lens. If, however, the materials, such as the cataractic lens, are too hard and massive to be aspirated through the aspiration line 114, then the distal end of the needle 110 is ultrasonically vibrated and applied to the material to be emulsified into a size and state that can be successfully aspirated.

Needle 110 is ultrasonically vibrated by applying electric power to the piezoelectric crystals 180, which in turn, cause horn 150 to ultrasonically vibrate and/or amplify the movement, which in turn, ultrasonically vibrates the needle 110. The electric power is defined by a number of parameters, such as signal frequency and amplitude, and if the power is applied in pulses, then the parameters can further include pulse width, shape, size, duty cycle, amplitude, and so on. These parameters are controlled by a control unit. An example of controlling such parameters is described in U.S. Pat. No. 7,169,123 to Kadziauskas, et al., which is hereby incorporated by reference in its entirety.

Vibration of needle 110 and horn 150 of handpiece 100 generates significant heat at the tip of the needle, which may damage tissue near the needle. This significant limitation is overcome by the present invention.

The present invention relates to using one or more MEMS devices to generate movement of a needle of a handpiece. MEMS devices integrate mechanical and electrical structures, sensors, and/or actuators on a silicon substrate using microfabrication. The combination of components allows a system to gather and process information, decide on a course of action, and control the surrounding environment. The benefits of such a device include increased affordability, functionality, and performance of products. MEMS work by sensors that measure mechanical, thermal, biological, chemical, magnetic, and/or optical signals from the environment. The microelectronic integrated circuits act as the "brains" of the system (the decision-making part of the system), by processing the information from the sensors; and the actuators help the system respond by moving, positioning, pumping, filtering, or somehow controlling the surrounding environment to achieve its purpose.

MEMS devices have a characteristic length between 1 micron and 1 mm. *MEMS: Design and Fabrication*, edited by Mohamed Gad-el-Hak, $2^{nd}$ Edition, November 2005, which is hereby incorporated by reference in its entirety.

There are different varieties of MEMS devices, including microsensors, micromotors, and microgears. Id. Current manufacturing techniques for MEMS devices include surface silicon micromachining (depositing thin films on the surface); bulk silicon micromachining (forming mechanical structures in the silicon substrates—etching through the wafer); lithography, electrodepositing, and plastic molding; and electrodischarge machining. Id.

According to an embodiment, using one or more MEMS devices, a needle of a handpiece can be oscillated to achieve similar movement of a needle of an ultrasound handpiece. Traditional deposition and lithography used in microchip design today can be applied to create a microchip attached to a needle of a handpiece that vibrates the needle in any desired direction, including, but not limited to, transversal (side-to-side), torsional, and longitudinal. In traditional deposition and lithography practices two dissimilar materials are used, commonly referred to as dopants. Dopants are deposited onto a wafer using a variety of techniques well known in the art. The dopants either have a positive or a negative charge; and the dopants are separated by a channel. Applying a voltage or current to one of the doped sides causes the other side to be attracted to the side where the current is applied. By removing the voltage or current from the same side causes the sides to move away. Repeating this application of voltage or current creates motion. In addition to electrostatic attraction and repulsion, other forms of generating force or movement using MEMS may be employed with the present invention, including but not limited to thermal and magnetic actuation.

The present invention also solves many problems associated with ultrasound phaco handpieces. First, using one or more MEMS devices to actuate the needle of a handpiece reduces manufacturing time and costs. These reductions also make it possible to manufacture a single use disposable handpieces that provide additional safety to the patient. Disposable handpieces may also reduce the amount of metal used with the handpiece. Second, using one or more MEMS devices enables finer control of the movement of the distal end of the needle, which promotes safer cataractic lens removal. Finer control allows for a safer procedure by preventing damage to tissue, including but not limited to tissue surrounding the incision, the capsular bag, and other structures of the eye that may be exposed to the needle of the handpiece. With MEMS, movement of the distal end of the needle is always a known quantity based on manufacturing processes. Without being limited to a theory, use of one or more MEMS devices coupled with a horn and/or a needle may cause the tip of the needle to oscillate and emulsify the lens by mechanical break down of the cataractic lens, e.g. a jackhammer. In an embodiment, multiple MEMS devices may be coupled with a horn and/or needle to cause the tip of the needle to move in a single direction and/or multiple directions. In an embodiment, 5 to 6 MEMS devices may be used for movement in a single direction or in multiple directions. Each MEMS device may provide any desired tip excursion, including but not limited to 1 mm to 2 mm.

MEMS devices of the present invention differ from standard ultrasonic handpieces in many ways, including the different phase angles and frequencies are removed and replaced with voltage and current for controlling velocity and direction.

Figure 2:
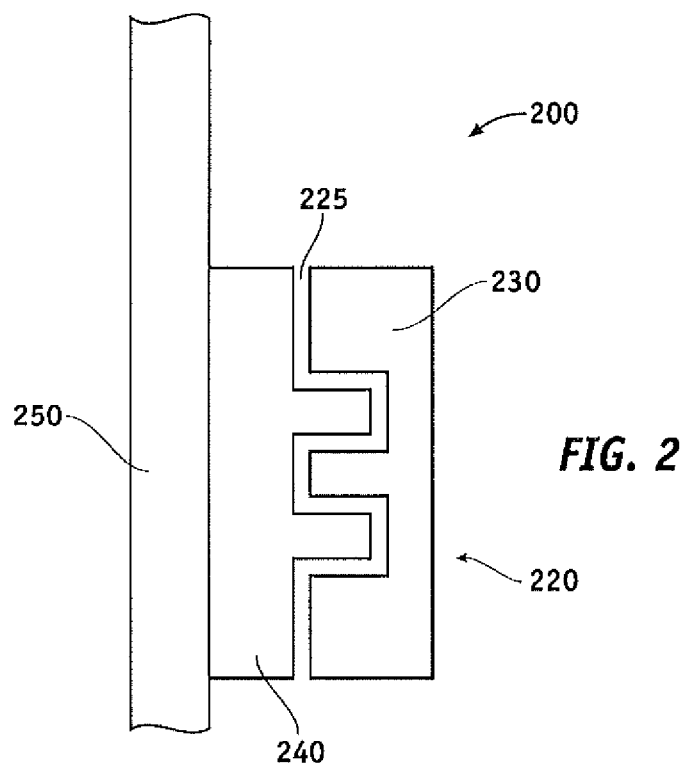
FIG. 2 is a plan view of an embodiment of a MEMS system.

FIG. 2 illustrates an embodiment of the present invention. MEMS system 200 includes MEMS device 220 and horn 250. MEMS device 220 comprises dopant side 240 and dopant side 230. Dopant side 240 or dopant side 230 may be positive or negative as long as one side is positive and the other is negative. Channel 225 is located between dopant side 240 and dopant side 230. The shape and/or size of channel 225, dopant side 230, and/or dopant side 240 may be changed to create different directions of movement.

Figure 3:
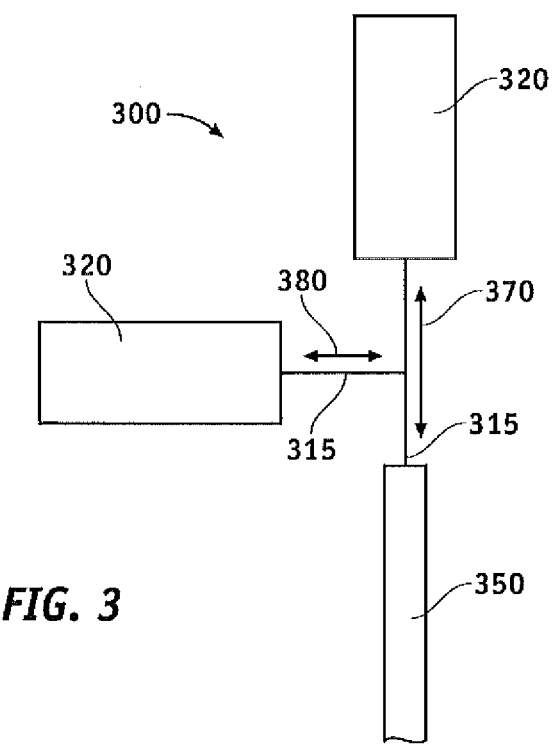
FIG. 3 is a plan view of an embodiment of a MEMS system.

FIG. 3 illustrates another embodiment of the present invention. In FIG. 3, MEMS system 300 comprises horn 350 and MEMS devices 320, wherein horn 350 is capable of being moved in at least two directions—transversal direction 380 and longitudinal direction 370. The movement of horn 350 causes a needle coupled with horn 350 to move in the same directions as horn 350. MEMS device 320 may be coupled with horn 350 via linkages 315. Each MEMS device 320 may be activated at the same time or at different times to achieve a desired movement of horn 350 and a needle coupled with horn 350.

Figure 4:
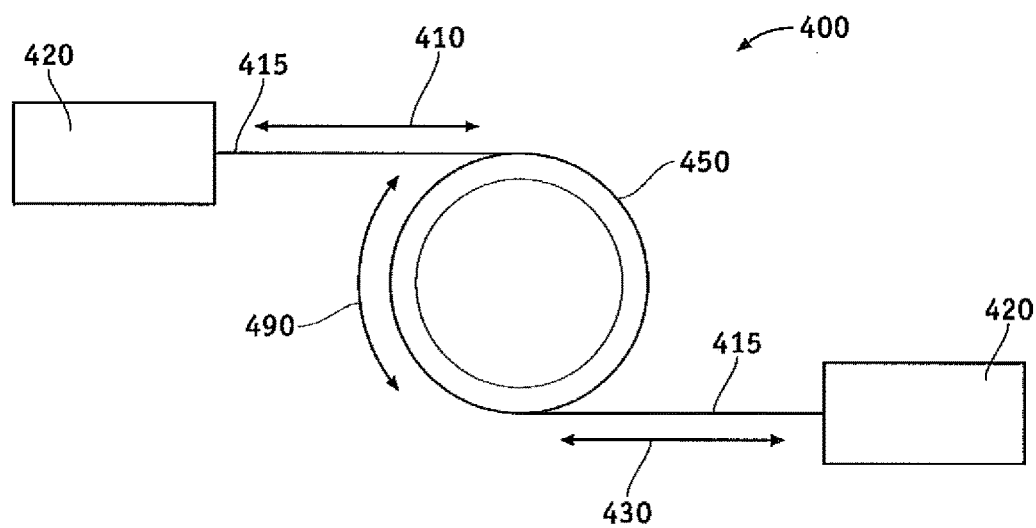
FIG. 4 is a bottom view of an embodiment of a MEMS system.

FIG. 4 illustrates another embodiment of the present invention. Specifically, FIG. 4 shows MEMS system 400. MEMS system 400 includes MEMS device 420 and horn 450. When MEMS devices 420 are activated, horn 450 is rotated along its longitudinal axis as shown by rotational direction 490. MEMS devices 420 may be coupled with horn 450 via linkages 415. MEMS devices 420 are capable of moving in directions 410 and 430. Movement of MEMS devices 420 in a normal direction to the longitudinal axis of horn 450 causes horn 450 to move in rotational direction 490.

Figure 5:
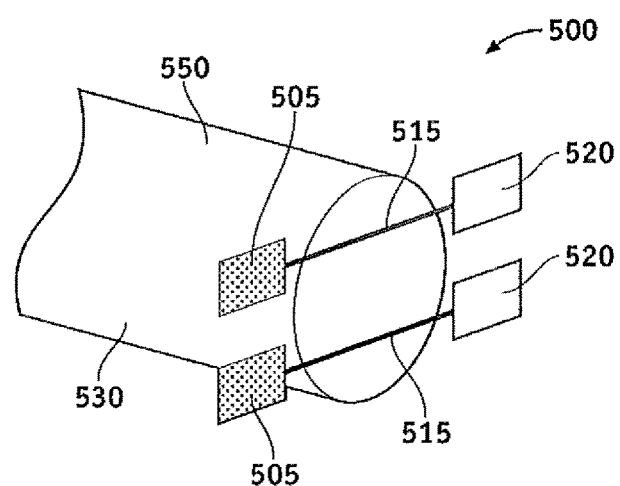
FIG. 5 is a side view of an embodiment of a MEMS system.

FIG. 5 illustrates another embodiment where MEMS devices 520 of MEMS system 500 are coupled with horn 550 via linkages 515 on the outer surface 530 of horn 550. One or more MEMS devices 520 may be coupled with outer surface 530 of horn 550. MEMS devices 520 may also be coupled with horn 550 via pads 505.

Figure 6:
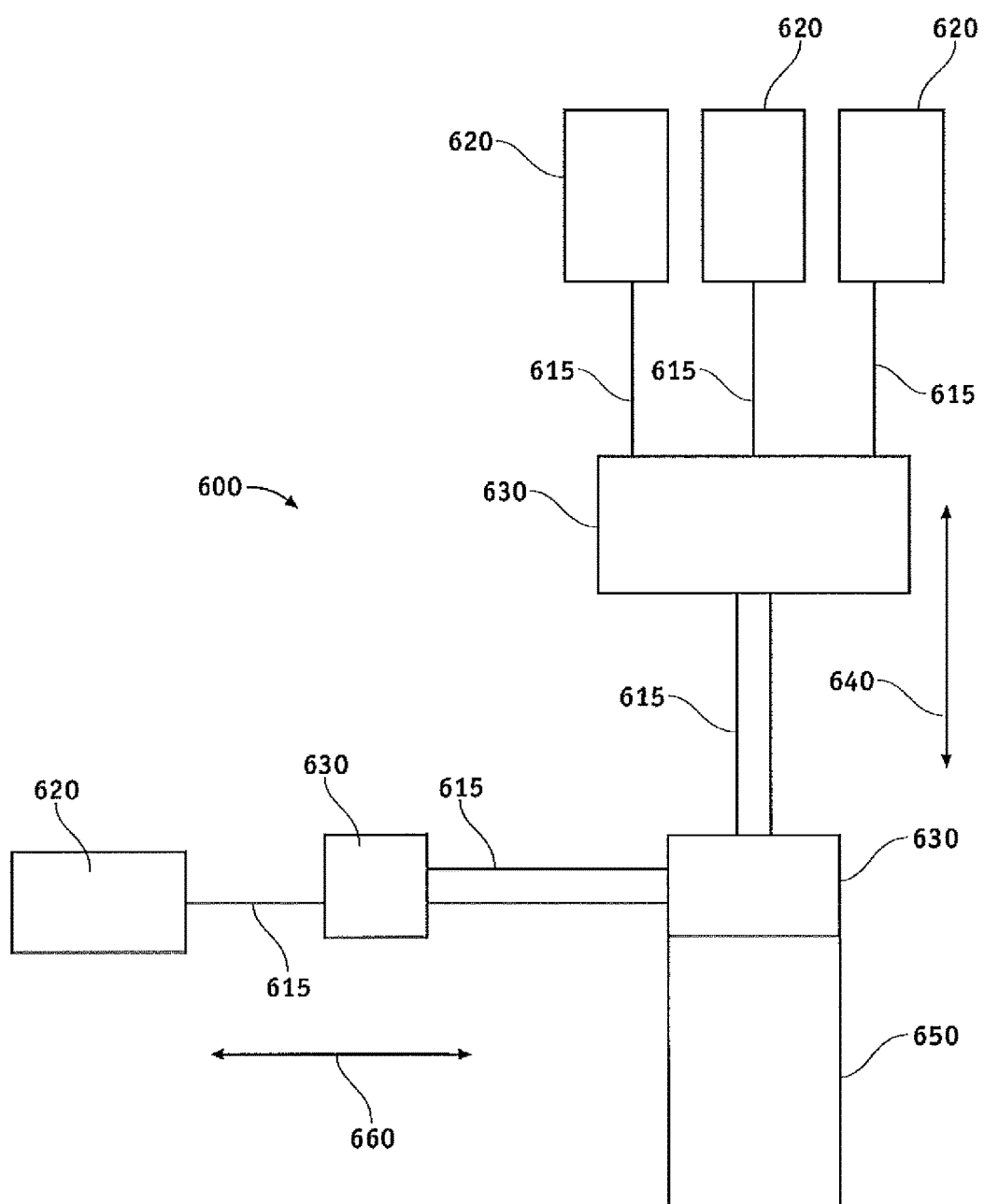
FIG. 6 is a plan view of an embodiment of a MEMS system.

FIG. 6 illustrates another embodiment where MEMS system 600 comprises multiple MEMS devices 620, multiple pads 630, and multiple linkages 615. Horn 650 may be coupled with multiple MEMS devices 620 to generate movement in multiple directions. As illustrated in FIG. 6, three MEMS devices 620 are coupled with horn 650 via linkages 615 and pad 630. These three MEMS devices 620 are capable of generating movement of horn 650 in longitudinal direction 640 (along a longitudinal axis of horn 650). One MEMS device 620 may be coupled with horn 650 via linkages 615 and pad 630. This MEMS device 620 is capable of generating movement of horn 650 in transverse direction 660 (perpendicular to a longitudinal axis of horn 650). Linkages 615 may be coupled with an outer surface or end of horn 650. Linkages 615 may also be coupled with a surface of pads 630. Linkages 615 may be of any shape or size. Pads 630 may also be of any shape or size to accommodate the use of one or more MEMS devices 620.

The linkages (315, 415, and 515) may be of any size or shape to enable coupling of one or more MEMS devices (220, 320, 420, and 520) with a horn (150, 250, 350, 450, and 550) and/or a needle. The linkages may couple one or more MEMS device with one or more pads (505), a needle, and/or horn by any orientation and on any location of the MEMS device, pads, and/or horn in order to achieve the desired directional movement, amount of movement, and design of the handpiece. The linkages may also be coupled directly with an outer surface of a needle or a horn. The linkage may be of any material known in the art, including but not limited to all ferrous and nonferrous metals.

In an embodiment, an asymmetric MEMS unit may be used. A single MEMS device may generate all of the movement required, including in an asymmetric fashion by asymmetrical coupling one or more linkages to the horn and/or needle. With one pulse through the MEMS device an expansion and contraction movement will happen. The amount of force may be increased or decreased depending upon the number of MEMS devices used for a particular directional movement.

According to another embodiment, the MEMS devices may also be used with a vitrectomy cutter. An example of a vitrectomy cutter is illustrated in U.S. Pat. No. 6,575,990 (Wang, et al.), which is hereby incorporated by reference in its entirety. Current vitrectomy cutters rely on air supply to generate the movement of the cutting blade to cut the vitreous. By using one or more MEMS devices to actuate the movement of the cutting blade, the problems associated with currently used vitrectomy cutters may be reduced, such as, but not limited to adjusting the air pressure depending upon the altitude at which the surgery is performed. Moreover, eliminating the air supply would make the machines more compact and portable, thereby reducing the overall cost of the machines.

Figure 7:
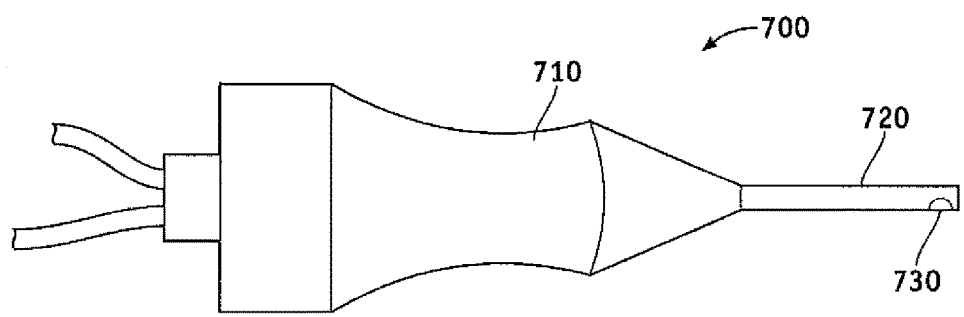
FIG. 7 is a plan view of a vitrectomy cutter.

In FIG. 7 a vitrectomy cutter known in the art is illustrated. Vitrectomy cutter 700 includes handle 710 coupled with needle body 720. Needle body 720 comprises one or more ports 730. Housed within needle body 720 is one or more blades 810 (see FIG. 8) that may pass over the one or more ports 730 of needle body 720, such that any vitreous that enters port 730 may be cut by the one or more blades 810. The one or more blades act as a guillotine.

Figure 8:
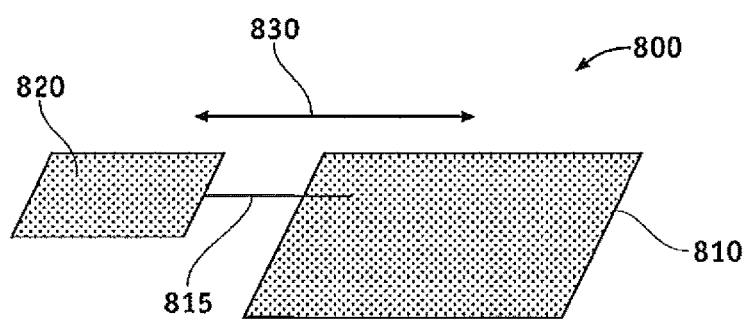
FIG. 8 is a plan view of an embodiment of a MEMS system.

In FIG. 8, a MEMS device system of the present invention is illustrated. MEMS device system 800 includes MEMS device 820 and blade 810. MEMS device system 800 may be housed within needle body 720 and/or handle 710. One or more MEMS devices 820 may be coupled with one or more blades 810. Activation of one or more MEMS devices 820 causes movement of blade 810 in direction 830 causing blade 810 to act as a guillotine to cut the vitreous. The MEMS devices may be coupled with the one or more blades directly or via a pad/linkage system as described herein. As shown in FIG. 8, blade 810 is coupled with MEMS device 820 via linkage 815. As discussed above, the linkages (e.g. 815) may be of any size or shape to enable coupling of one or more MEMS devices (820) with blade 810 and/or one or more pads.

MEMS devices of the present invention may be made of any material known in the art, including but not limited to polycrystalline silicon. The size of the MEMS devices may be of any size and shape that provides the necessary movement of the needle and fits within a standard sized handpiece, handle, and/or needle body.

As described herein, one or more MEMS devices may be coupled with a needle instead of a horn. In some embodiments, a needle and a horn may be one unit and referred to as a horn or a needle.

The present invention provides more reliability and is more cost effective due to the manufacturing process, e.g. cmos manufacturing, resulting in less failures and returns. In an embodiment, a phacoemulsification handpiece has one or more MEMS devices and is disposable. A disposable handpiece would reduce the need for sterilization and minimize the risk of cross-contamination.

All references cited herein are hereby incorporated by reference in their entirety including any references cited therein.

Although the present invention has been described in terms of specific embodiments, changes and modifications can be carried out without departing from the scope of the invention which is intended to be limited only by the scope of the claims.

The invention claimed is:

1. A phacoemulsification handpiece, comprising:
a needle, wherein the needle comprises a lumen configured for aspiration;
a horn coupled to the needle;
a microelectromechanical system (MEMS) device coupled to the horn that includes:
a first member and a second member that is separated from the first member by a channel, the first member and the second member being configured to have opposite charges,
wherein applying a voltage or current to the second member causes the first member to be attracted to the second member, thereby causing the needle to vibrate.

2. The phacoemulsification handpiece of claim 1, wherein the needle is vibrated in one of a transversal direction, torsional direction, and longitudinal direction, along a longitudinal axis of the needle.

3. The phacoemulsification handpiece of claim 1, wherein one of the first member and the second member includes a positive dopant and the other one of the first member and the second member includes a negative dopant.

4. The phacoemulsification handpiece of claim 1, wherein removing the voltage or current causes the first member to move away from the second member.

5. The phacoemulsification handpiece of claim 1, wherein the second member has a sidewall adjacent to a sidewall of the first member.

6. The phacoemulsification handpiece of claim 5, wherein the sidewall of the second member adjacent to the sidewall of the first member has a shape that is complementary to the sidewall of the first member.

7. The phacoemulsification handpiece of claim 1, wherein the second member is coupled to the horn.

* * * * *